United States Patent [19]
Gottlieb

[11] Patent Number: 4,468,379
[45] Date of Patent: Aug. 28, 1984

[54] LEUKOCYTE EXTRACTS FOR AFFECTING THE IMMUNE SYSTEM

[75] Inventor: A. Arthur Gottlieb, New Orleans, La.

[73] Assignee: Endeavor Corp., New Orleans, La.

[21] Appl. No.: 441,432

[22] Filed: Nov. 15, 1982

Related U.S. Application Data

[63] Continuation-in-part of Ser. No. 256,886, May 6, 1982, abandoned, which is a continuation-in-part of Ser. No. 149,737, May 14, 1980, abandoned.

[51] Int. Cl.$^3$ ............................................. A61K 35/14
[52] U.S. Cl. ..................................... 424/101; 424/88
[58] Field of Search .................................. 424/101, 88

[56] References Cited

PUBLICATIONS

Wotila–Transfer Factor & Other Immunological Activities of Human Leucocyte Dialysate and Other Dialysates of Mammalian Tissues (1979), pp. 2-4, 6-7, 12-17, 22-23 and 25-27.

Primary Examiner—Sam Rosen
Attorney, Agent, or Firm—Richard H. Stern

[57] ABSTRACT

A group of substances derived from human leukocytes (white blood cells) are described that amplify, suppress, or otherwise modulate the response of the immune system to reintroduction of antigens. The described materials are generically effective as to antigens rather than specific as to particular antigens, but the described modulators of immune response are effective only in respect of antigens with which the recipient has previously been challenged. The described materials are extracted from leukocyte dialysates by processes involving high pressure liquid chromatography with specified resin/solvent systems. Uses and pharmaceutical compositions for use of the materials are also described.

43 Claims, 4 Drawing Figures

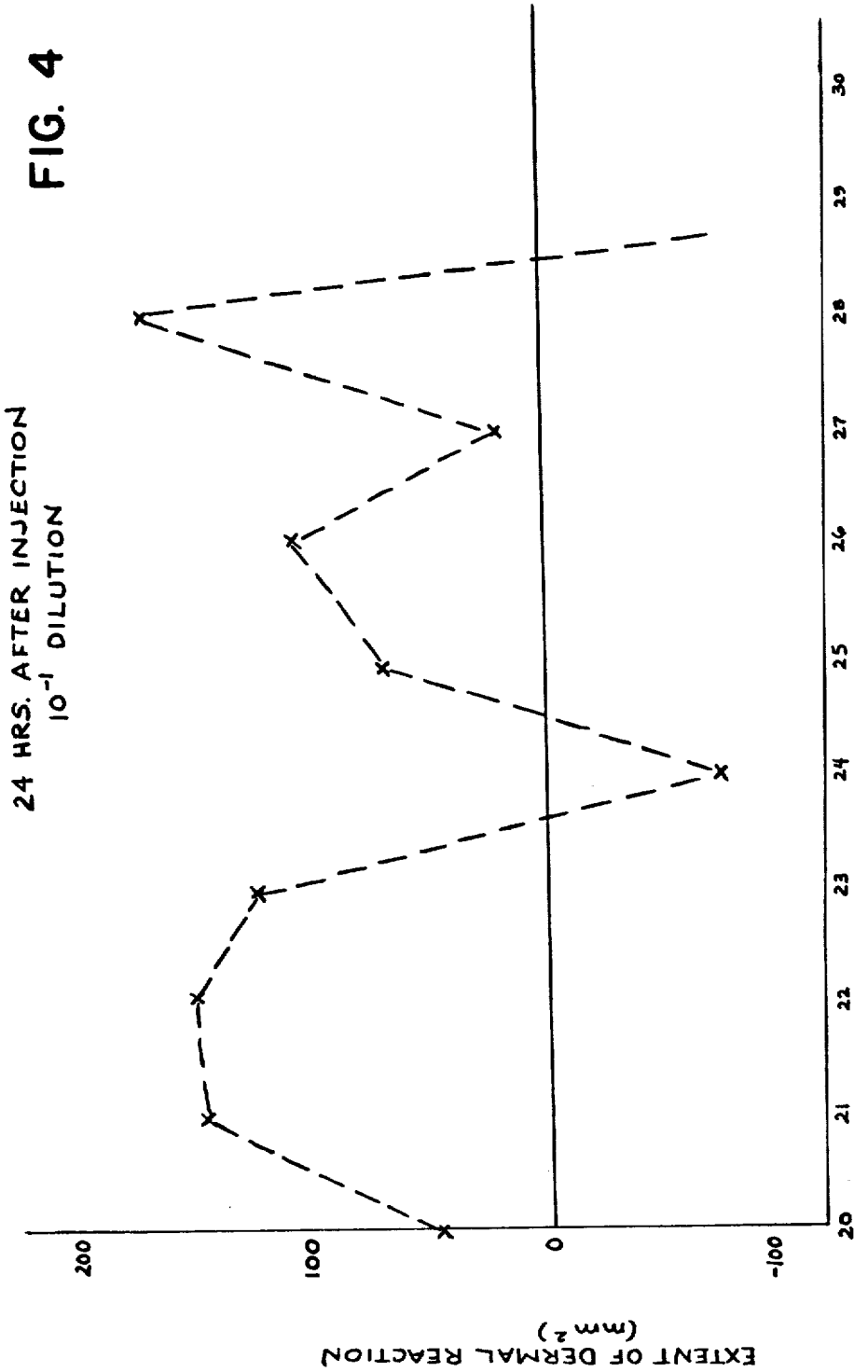

LEUKOCYTE EXTRACTS FOR AFFECTING THE IMMUNE SYSTEM

This application is a continuation-in-part application based on copending application Ser. No. 256,886, filed May 6, 1982, which is a continuation-in-part application based on then copending Ser. No. 149,737, filed May 14, 1980, both now abandoned.

BACKGROUND OF THE INVENTION

The human immune system is highly complex and at present imperfectly understood. It is presently considered to have two principal aspects: (1) humoral immunity, which is mediated by circulating antibodies; and (2) cell-mediated immunity, which, as the name implies, is mediated by cells, viz., lymphoid cells. Humoral immunity is transferred from an immune donor to a non-immune recipient by means of serum immunoglobulins. Such serum-mediated transfers result in immune responses that are manifest almost instantly. Cell-mediated immunity is transferred by means of peripheral blood leukocytes, and such immune responses develop slowly, over a period of several hours. The present invention concerns cell-mediated immunity.

A typical manifestation of cell-mediated immunity is the delayed hypersensitivity ("DH") skin reaction. A DH skin reaction is observed when the appropriate antigen is injected subcutaneously. Within 24 to 48 hours, local inflammation (erythema) and a swelling and thickening (induration) are observed in a sensitive individual. The degree of sensitivity may be measured by the size and severity of the reaction. The DH reaction also presents characteristic histological findings, specifically, perivascular infiltration of lymphocytes and monocytes in the inflamed area. The cells seen at the site of a DH reaction are derived from the peripheral blood leukocyte population.

The mechanisms of cell-mediated immunity are as yet incompletely understood. It is known that the cells which mediate the response are capable of responding in a variety of ways to an antigenic challenge. These responses include: proliferation of cells bearing specific sensitivity to a given antigen; the induction and multiplication of cells mediating a variety of immune functions, including antibody production; and reactions against foreign cells and tumors. The quality and quantity of these response patterns is affected by many factors, including (1) hormones of the thymus and adrenal cortex; (2) interferons; and (3) other effectors of cellular responses, including histamine, serotonin, and the prostaglandins.

The present invention relates to the discovery of modulators of the immunity system, isolated from dialyzed extracts of leukocytes; profoundly affecting the quality and quantity of cell-mediated immunity responses; useful in the treatment of a variety of clinical conditions characterized by overreaction or by inadequate reaction to a specific antigen; and useful in the alleviation of certain anergic conditions.

PRIOR ART

In 1954, H. S. Lawrence reported that a lysate prepared from the leukocytes of tuberculin-sensitive donors could transfer that sensitivity to tuberculin-nonreactive recipients. *Journal of Clinical Investigation,* 33:951 (1954). For a later review of that work, see Lawrence, H. S., *The Harvey Lectures,* 68:239 (1974). For collections of state of the art papers, see *Transfer Factor: Basic Properties and Clinical Applications,* M. S. Ascher, A. A. Gottlieb [the applicant], and C. H. Kirkpatrick, Eds., Academic Press, Inc., New York (1976), and *Immune Regulators in Transfer Factor,* A. Kahn et al., Eds. Academic Press, Inc., New York (1979). The transfer of sensitivity on which Lawrence reported was presumed to be due to a factor in the leukocyte lysate that was later given the operational term "transfer factor." See Lawrence, H. S., commenting on paper of Najarian, J. S., and Feldman, J. D., in *Cell-Bound Antibodies* (B. Amos and H. Koprowski, Eds.).

The "transfer factor" phenomenon is demonstrable only in human beings. Consequently, research progress in isolating and characterizing the active principle has been slow. To demonstrate transfer factor, two patients must be identified, (1) a donor, known to display a DH reaction to a given antigen, and (2) a recipient, known to give no DH reaction when challenged with the same antigen (and therefore presumably lacking cell-mediated immunity to that antigen). Leukocytes prepared from the blood of the donor are disrupted, and the cell contents dialyzed. The concentrated dialysate, in a suitable buffer, is injected subcutaneously in the forearm or other convenient location of the recipient. After about two days, the recipient is then challenged by a subcutaneous injection of the antigen at the same or another location. A typical DH reaction can be observed about one week later. Immunity thus transferred reportedly may persist in the recipient for as long as two years.

Progress in fractionating and characterizing transfer factor has been impeded by the lack of associated structural or chemical criteria and by the fact that the phenomena observed after fractionation are often qualitatively different from the phenomena induced by the original dialysate. Although the term "transfer factor" appears in literature as applied to fractionated preparations, and as monitored by criteria other than a DH skin response, it is unclear whether in such terminology the term "transfer factor" is indeed used to refer to a single biochemical entity or to an activity that represents a single biological function, or rather to refer to a mixture of materials of various kinds. As used herein, the term "transfer factor" is restricted to the crude leukocyte dialysate as isolated by Lawrence and having an activity as originally characterized by Lawrence, i.e., the ability to transfer immunity to a specific antigen from a highly sensitive donor to a non-sensitive recipient. Such dialysate may, and the inventor believes that it does, contain various different molecules and entities.

Prior art fractionation of human transfer factor has demonstrated the presence of a variety of active materials. Vandenbark, A. A., et al., *J. Immunol.* 118:636 (1977), reported the results of chromatography of the dialysate of leukocyte extracts on Sephadex G-25 (trademark of Pharmacia, Inc., Uppsala, Sweden). Biological activity in vivo was found only in association with two major peaks of optical density at 254 nm or 280 nm. One such peak fraction was reported to transfer significant skin test reactivity from antigen-responsive donors to previously non-reactive recipients. The other peak fraction produced spontaneous activity (a dermal response without added antigen) and also significantly increased dermal response when combined with antigen. The peak fractions were further fractionated by isoelectric focusing and by reverse phase chromatography using a solvent system of one percent acetic acid or five percent methanol on a column bed packed with octadecyl silane resin. However, results of biological activity tests followed subfractionation were not reported.

Gottlieb, A. A., et al., in *Transfer Factor: Basic Properties and Clinical Applications*, at page 263, introduced the use of fluorescamine (also termed "Fluram", trademark of Hoffman-LaRoche, Inc., Nutley, N.J.), as a means for monitoring the fractionation of leukocyte dialysates. Fluorescamine reacts with substances containing primary amino groups to yield highly fluorescent products, providing a highly sensitive assay for proteins and other compounds bearing primary amino groups. Bohlen, P., et al., *Arch. Biochem. Biophys.*, 155:213 (1973). The dialyzable leukocyte extract material was fractionated on a Sephadex G-10 (trademark of Pharmacia, Inc., Uppsala, Sweden) column. Biological activity was found associated with a major fluroescamine-reactive peak. DH reactions were observed whether or not antigen was added, although response was somewhat greater in the presence of antigen.

Dialyzable leukocyte extracts were further fractionated by Gottlieb, A. A., et al., as reported in *J. Reticuloendothelial Soc.*, 21:403 (1977). The extracts were first subjected to differential molecular weight ("M.W.") dialysis, using dialysis membranes having nominal M.W. cutoffs of about 12,000 and about 3500, respectively. Material passing through the latter membrane, having a M.W. range generally less than 3500, was termed the "S" (for "small") fraction, while material in the general M.W. range of 3500 to 12,000 was designated the "L" (for "large") fraction. Both fractions were subjected to gel filtration on Sephadex G-10. Biological activity was again associated with the fluorescamine-reactive peak fractions. However, the activity did not appear to be a function of the immunologic state of the donor.

In addition, two distinguishable effects were observed. The first was an induction of DH response *in the absence of stated antigen and independent of the immunologic state of the donor or recipient*. Such activity is referred to herein as "inducer," as defined below. The second activity was the ability to augment intradermal reactions to antigens to which the recipient was sensitive but not to antigen to which the recipient had no prior exposure. This augmentor activity *was found in the fluorescamine-reactive chromatographic fractions*, and appeared to augment the recipient's DH response to an antigen to which he was already sensitive. In both instances, the sensitivity of the donor appeared irrelevant.

Additional fractionation of the S fraction on hydroxylapatite chromatography showed that the biological activity producing a DH response in the absence of added antigen was not associated with the main polypeptide fraction, as measured by reaction with fluorescamine.

Additional data were presented by Gottlieb, A. A., et al., in *J. Immunol.*, 124:885 (198), on the fractionation, by means of a long, 150 cm. Sephadex G-10 column, of "inducer" materials (those producing a DH reaction in the absence of added antigen) and "amplifier" materials (those producing a DH reaction in the presence of antigens to which the recipient is known to be sensitive). The amplifier materials were reported as remaining associated with the main fluorescamine reactive fractions, while the inducer materials were not. It was further reported that the materials having "amplifier" activity remained associated with the fluorescamine-reactive peak, upon further fractionation on hydroxylapatite. Controlled studies demonstrated that the reported activities were not found in similarly treated lysates of red blood cells, nor was any activity associated with a saline solution processed according to the same purification procedure.

Gottlieb, A. A., et al., *Immune Regulators in Transfer Factor* (A. Kahn, C. Kirkpatrick, and Hill, Eds., Accademic Press, Inc., New York, 1979), page 339, in a report unaccompanied by data, suggested that material having an additional activity, termed "suppressor", could be separated by hydroxylapatite chromatography from material having an "augmentor" activity. The "augmentor" material was found in the S dialysis fraction (M.W. under 3500) and was always associated with the major fluorescamine-reactive peak. The "augmentor" fraction was thought to be systemically effective in previously BCG-exposed anergic patients. In addition, a "suppressor" activity found in the L dialysis fraction (M.W. between 3500 and 12,000) was stated to elute at a higher salt concentration than the fluorescamine-reactive material, on hydroxylapatite chromatography.

In another study where dialyzed leukocyte extracts were fractionated, Wilson, G. B. et al., *J. Lab. Clin. Med.*, 93:819 (1979), reported four activities affecting in vitro leukocyte migration: two antigen-independent activities (producing a response in the absence of any antigen), an antigen-dependent specific inhibitor, and an antigen-dependent enhancer. The antigen-dependent inhibitor had properties in common with "transfer factor" since only antigen of the appropriate donor specificity caused significant inhibition of in vitro leukocyte migration. The antigen-dependent enhancement of leukocyte migration was not characterized with respect to antigen specificity. That activity, however, is not known to have any relationship to any in vivo function of the human immune system nor any predictable therapeutic utility.

Some of the foregoing work was summarized and commented on by A. Uotila, in *Transfer Factor and Other Immunological Activities of Human Leukocyte Dialysate and Other Dialysates of Mammalian Tissues* (1979). Uotila's monograph indicates that preparations of so-called "transfer factor" may contain a large variety of substances. Uotila suggests that an "augmenting activity" can be derived from dialyzable leukocyte extends ("DLE") in guinea pigs, but does not disclose whether this is one or several different materials or activities, or if the latter, how to separate them from one another. Uotila also suggests that "augmenting activity" and "transfer factor" are similar substances, and possibly the same molecules. Uotila found alleged similarities in enzymatic sensitivity between chemical compounds in human "transfer factor" materials and guinea pig "augmentor activity" materials. It is believed that this monograph is of interest because it teaches away from the disclosure of the instant patent application.

SUMMARY OF THE INVENTION

This invention relates to modulators of the human immune system. A "modulator" as herein defined is, in general terms, any substance or material that affects a response, whether direct or indirect, of an animal or human body, portion thereof, or matter taken therefrom, to reintroduction of antigens to which said body has been previously exposed, where such response is specifically attributable to the function of the immunity system of said animal or human. A narrower and more precise definition of the term is used subsequently, after further characteristics of the present invention are explained. Generally, as used herein, the term "modulator material" refers collectively or generically to material having modulator activity and containing one or more particular materials ("species") causing such activity, while the term "modulator" refers specifically to one of the approximately eight particular, extractable materials ("species") having an activity described herein.

Substances having general bodily effects that may also include effects on the immune response are not subsumed within the term "modulator," as herein defined. The modulators described herein manifest their activity in a DH skin reaction test, and therefore appear to exert their primary effect on the cell-mediated immunity system. It will be understood, however, that the described modulators have broad effects on the entire immunity system, and may also affect the humoral immunity system.

For purposes of discussion herein, the term "transfer factor," "inducer," "amplifier," and "suppressor" are each defined, below, in terms of their respective activities in regard to affecting a DH response in a skin reaction.

The term "transfer factor" denotes a dialysate of a crude leukocyte extract, as described above. A "transfer factor activity" is manifest when the transfer factor preparation is made from leukocytes of a donor known to be sensitive to a given antigen and is injected subcutaneously into the skin of a recipient known to be insensitive to the same antigen. The recipient is challenged, at a later time, with the antigen, and a DH response is observed. Normally, the recipient, in the absence of the injected transfer factor activity, would have been unresponsive.

It will be understood that transfer factors are *not* modulators, as defined above, since the effect of a transfer factor is observed in a recipient who has *not* previously been exposed to a given antigen, while the effect of a modulator is observed only upon or following reintroduction of an antigen to which the recipient was previously exposed. Furthermore, transfer factor effects are *specific* with respect to a given antigen, but the amplifiers and suppressors herein described exert *nonspecific* effects with respect to *any* antigen to which the recipient was previously exposed.

"Inducer" is defined as that material producing a DH response in the absence of added antigen and irrespective of the sensitivities of donor and recipient. Inducer materials are also, therefore, not modulators.

"Amplifier" material is that modulator material characterized, in general terms, by "amplifier" activity, i.e., the production of a greater than normal response (faster or stronger, or both) in a sensitive recipient, following injection of the antigen to which the recipient is sensitive. Amplifier activity is not dependent upon the specific immunological sensitivity of the donor.

"Suppressor" material is that modulator material characterized by "suppressor" activity, which is, in general terms, that modulator activity observed in a sensitive recipient when the suppressor material is injected and an antigen to which the recipient is already sensitive is injected at the same time or soon thereafter, with the result that the recipient manifests a less than normal (slower or weaker, or both) response.

In the present invention, eight specific modulators of the human immune system have been isolated from dialysates of leukocyte extracts. Six such modulators described herein have amplifier activity and two have suppressor activity. Amplifier material is considered useful in the treatment of anergic conditions and conditions of immune hyposensitivity, both local and systemic, while suppressor material is considered useful for the preparation and treatment of local hypersensitivity conditions, such as poison ivy. These six amplifiers are designated amplifiers 1-6. These two suppressors are identified as the S-suppressor and the L-suppressor.

FIG. 4 is a graph of a human dermal reaction to antigen, showing the degree and kind of modulator effect associated with the various fractions of purified leuokocyte extract.

DETAILED DESCRIPTION OF THE PREFERRED EMBODIMENT

Figure 1:
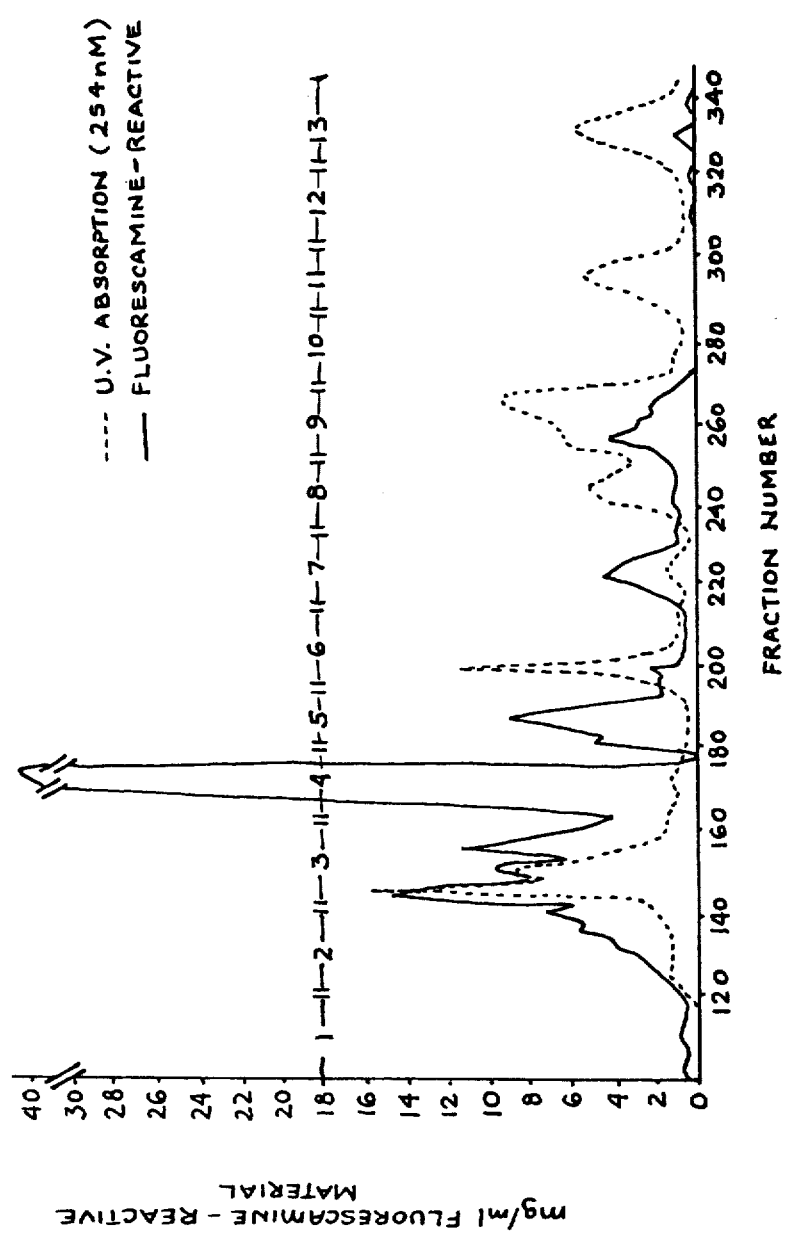
FIG. 1 is a graph showing the amount of fluorescamine reactive material in various fractions separated in the course of a gel filtration of the S-fraction of a leucocyte extract; the solid line indicates fluorescamine reactive material.

A principal contribution of the present invention lies in the discovery of substances that modulate immune responsiveness. Present techniques have permitted identification of modulators which amplify or suppress the magnitude or rapidity of response to antigens to which an individual human being has been previously exposed. However, it is evident that a variety of other modulating functions are or may be manifested by such substances, including duration of response, threshold of sensitivity, and type of response, such as inflammatory, proliferation of lymphocytes or production of circulating antibody. Clearly, such modulating functions will be defined in terms of the test system used to detect and measure them. The modulators of the present invention include not only amplifiers and suppressors of a DH response, but also such other manifestations of immune modulation as may be detected and measured in other appropriate test systems.

The modulators herein described are therefore but part of a system or modulator substances which constitute a natural means of intercellular communication between components of the animal (including human) immune system, whereby the state of immune responsiveness is continually monitored and modified in the body in accordance with the level and activity of current antigen challenge to the body. Therefore, further modulators are likely to be discovered, now that it is understood from the present invention that such a system of modulators exists. Further investigation, employing other purification techniques and other test procedures, will result in the identification and purification of such further modulators. The present invention paves the way for such discoveries, by making known to the art the existence of such modulators and by pioneering the isolation and characterization of eight specific modulators having new and unexpected properties useful for treatment of a variety of immunity-related conditions.

In the following discussion, procedures are described wherein materials were obtained from human donors and test measurements were made on human recipients. The procedures and reagents used herein were chosen to provide sterile and non-toxic products for human treatment. The sensitivities of donors and recipients to selected antigens were tested in advance.

The initial step in the preparation of the modulator material of this invention is preparation of leukocyte pellets, followed by separation of the small M.W. (under 3500) and large M.W. (3500 to 12,000) fractions of leukocyte extract of interest herein.

Table 1 shows a human dermal response to an antigen and various fractions of purified leukocyte extract material, at 7, 12, and 24 hours after injection of the antigen and said material. Table 2 shows a human dermal response to antigen and the "L" fraction of leukocyte extract material 25 and 43 hours after injection. Table 3 shows the dermal response of two different recipients to antigen and the same fractions of leukocyte extract material derived from a single donor, showing the absence of so-called "transfer factor" effects. Table 4 shows human dermal responses to antigen and various dilutions of various fractions of extract material. Table 5 shows human dermal responses (in a patient having sarcoidosis) to antigen and various dilutions of the modulator designated as Amplifier 6, illustrating amplified immune response to antigen as a result of use of Amplifier 6. Table 6 shows degree of activation of the patient's lymphocytes in vitro as a result of administration of Amplifier 6 to the patient.

EXAMPLE 1

Preparation of Leukocyte Pellet

Leukocytes were prepared by standard methods, employing either fractionation of whole blood samples or leukophoresis. In the former method, a 450 ml sample of whole blood was fractionated by sedimentation to separate red blood cells from leukocytes at $1 \times g$ in Macrodex (trandemark of Pharmacia Corporation, Piscataway, N.J., for 6% (W/V) Dextran 70 in normal saline). Approximately $1-2 \times 10^9$ leukocytes were recovered by this method.

Leukophoresis was preferred for obtaining larger amounts of cells, using a cell separator (Haemonetics Model 30S, Haemonetics Corp., Braintree, Mass.). The system was primed with 30 cc of 46.7% trisodium citrate (Haemonetics, Braintree, Mass.) and 500 ml of 6% (W/V) Volex (trademark of McGaw Co., Irvine, Calif.), which is a high-molecular-weight starch preparation used to enhance recovery of leukocytes from the peripheral blood and removal of red blood cells from the final leukocyte preparation by sedimentation.

In either method, leukocyte-rich plasma was obtained following a 60-minute incubation at 37° C. The leukocytes were recovered from the plasma by centrifugation at $400 \times g$ for 15 minutes followed by three washes with 0.15M saline. After washing, the leukocyte pellet was stored frozen at $-20°$ C. An average yield of leukocytes from six passes in the cell separator was $1 \times 10^{10}$ cells.

EXAMPLE 2

Dialysis of Leukocyte Extracts

Leukocyte extracts were prepared under sterile conditions, as in Example 1. Leukocyte pellets were resuspended in 10 ml of 5 mM ammonium bicarbonate, then subjected to 10 cycles of freeze-thawing in a dry ice and acetone bath. The lysate was first dialyzed against 5 mM ammonium bicarbonate, using cellulose dialysis tubing having a nominal 12,000 M.W. cutoff (Arthur H. Thomas, Inc., Chicago, Ill.). The retentate of the dialysis is discarded. After three changes of buffer, the combined dialysates were lyophilized, redissolved in a small volume of ammonium bicarbonate, and dialyzed in cellulose tubing of nominal 3500 M.W. cutoff, against 5 mM ammonium bicarbonate, as before. The retentate from the second dialysis, termed the "L" (for "large" M.W.) fraction herein, and the dialysate, termed the "S" (for "small" M.W.) fraction herein, were each lyophilized and stored frozen at $-20°$ C. until further use.

EXAMPLE 3

Ultrafiltration of Leukocyte Extracts

As an alternative to dialysis, the inventor has found ultrafiltration to be an expedient technique. The protocol for this technique begins with leukocyte pellets, as in Example 2. An equal volume of 5 mM ammonium bicarbonate solution is added to the leukocyte pellet. The resultant mixture is freeze-thawed 10 times in a dry ice/acetone bath. The volume of the mixture is then adjusted to 50 ml by addition of ammonium bicarbonate solution, and centrifuged at 1200 rpm for 6 minutes at 4° C. The supernatant is saved; the pellet is resuspended in 5 mM ammonium bicarbonate solution and washed three times. The washes are added to the original supernatant.

The pooled supernatant is filtered through an HP10-8 Amicon hollow fiber cartridge (Danvers, Mass.) having a M.W. cutoff of 10,000, at a flow rate of 70-80 ml/min. The supernatant is continuously recycled through the Amicon hollow fiber cartridge until about 20 ml remain. The ultrafiltered fraction, having M.W. less than approximately 10,000, is recovered and lyophilized. The material of M.W. more than approximately 10,000 is discarded. The resultant ultrafiltered fraction is freeze-dried, as before, and the product is subjected to dialysis against a dialysis membrane having a M.W. cutoff to about 3500. The resulant dialysate is the "S" fraction—the retentate is the "L" fraction. (The 12,000 M.W. cutoff of the membrane and 10,000 M.W. cutoff of the filter do not make a material difference in this process.)

As used herein, the term "dialysis" applies to either of the above procedures, described in Examples 2 and 3, or any other equivalent means of separating large and small molecules. When the hollow fiber cartridge is used, references to the nominal M.W. cutoff of the dialysis membrane must be understood as references to the nominal M.W. cutoff of the hollow fiber cartridge; and similar equation of retentate and dialysate to ultrafiltered fraction and supernatant must be made.

The next step in the preparation of modulator material is gel filtration of the S fraction, to purify the material of interest from other material, and to separate the S-fraction material into a number of separate fractions having different elutability characteristics.

EXAMPLE 4

Gel Filtration

Sephadex G-10 (trademark of Pharmacia, Inc., Uppsala, Sweden) was swollen overnight in 5 mM ammonium bicarbonate, then autoclaved. After removal of the fines, a 1.5 cm × 151 cm column was prepared and equilibrated in 5 mM ammonium bicarbonate. The column was loaded with 400 mg of fluorescamine-reactive material of the redissolved S fraction of Example 2 (based upon bovine serum albumin as the assay standard, according to the method of Bohlen, P., et al., Arch. Biochem. Biophys., 155:213 (1973)). The sample was eluted with 5 mM ammonium bicarbonate at a flow rate of 13 ml/hr. One total column volume (254 ml) was collected in 0.75 ml fraction and they were set aside.

Assay of Fractions

Ultraviolet absorption at 254 nm and fluorescamine reactivity, based upon 100 microliter aliquots, were measured on the fractions of Example 4. The results are shown in FIG. 1. A major fluorescamine-reactive peak was observed. The pattern was essentially constant from one individual donor to another.

The location of modulator activities of the fractions, in relation to the fluorescamine reactivity was discovered by assays ("modulator assays") of DH response over a series of 10-fold dilutions. The nature of the DH response varied in an unexpected manner with dilution. Undiluted samples in the region of the fluorescamine peak gave a reduced DH response to an antigen relative to the control response to antigen alone. Surprisingly, at dilutions of $10^{-2}$ and $10^{-3}$, amplification of the DH response, relative to the control, was observed. Even more surprisingly, at dilutions of the order of $10^{-5}$, suppression of the DH response was observed.

The fractions displaying such unusual response properties (termed "modulator-assayed" fractions herein) were selected and subjected to additional purification described below. From such experiments, the materials of interest ("modulator-assayed" materials) were located in a region containing the major fluorescamine-reactive peak and a smaller fluorescamine-reactive peak preceding the major fluorescamine-reactive peak. For subsequent purification steps, fractions 152 through 178 (shown in FIG. 1) were pooled and lyophilized. The possibility exists that final yields can be improved by pooling additional fractions on either side of those chosen. The optimal choice of fractions is not as yet determined.

In some experiments, gel filtration was carried out using a shorter (80 cm) column of Sephadex G-10. The results were comparable, except that the longer column gave improved resolution. In particular, an antigen independent inducer was separated from the main fluorescamine-reactive peak on the longer column.

As an alternative to gel filtration, purifications can be carried out by high-performance gel exclusion chromatography, using a 1×25 cm column of sulfonated polystyrene divinyl benzene having a 5000 M.W. exclusion limit (Shodex S-802/S, manufactured by Showa Denko KK, Tokyo, Japan), eluted with water at the rate of 0.8 ml/min. The term "gel filtration" as used herein should therefore be understood to include the foregoing equivalent purification means and other equivalents.

Reverse Phase Chromatography

Further purification of the material of Example 4 was carried out by reverse-phase high pressure liquid chromatography ("HPLC") using an octadecyl silane ("O.S.") resin column eluted with a 0 to 100% (v/v) gradient of ethanol in water. (All percentage references to ethanol-in-water gradients herein are on a v/v basis.)

The inventor has used two different versions of the HPLC process, with two respective O.S. columns. The first method was with a 0.26 cm (I.D.)×25 cm "analytic column" packed with Perkin-Elmer ODS-HC-SIL-X-1 octadecyl silane resin. To achieve greater output, the second method used a 2.3 cm (I.D.)×28 cm "preparative column" packed with the same O.S. resin. Both columns were used with a Series 3B Perkin-Elmer high pressure liquid chromatograph, but the elution characteristics of the two columns differ substantially, as explained below.

The Perkin-Elmer Series 3B High Pressure Liquid Chromatograph can be programmed to operate at a specified flow rate, such as 0.5 ml/min. Samples can then be collected at 2.0 minute intervals. The 0% to 100% ethanol-in-water gradient can be programmed to run, for example, from 0% to 100% ethanol in 60 minutes. This, in principle, divides the gradient into 30 2-minute intervals, during each of which a 1.0 ml sample is collected. Each such 1.0 ml sample should, in principle, represent a 100/30 or 3.33% change in ethanol concentration. The visual display of the Perkin-Elmer machine shows the ethanol concentration going into the column in accordance with the foregoing data.

However, the actual ethanol concentration in the effluent from the column (as measured by refractive indices of effluent calibrated against a standard curve of ethanol in water) appears, in the earlier portions of the gradient, to be substantially less than the concentration of ethanol being programmed (at that moment) into the machine. For example, in the "analytic column" procedure, at a flow rate of 0.5 ml/min, the display of the Perkin-Elmer machine indicates an apparent concentration of ethanol of 45% when the concentration in the effluent is actually 36%. In the "preparative column" procedure, at a flow rate of 5.0 ml/min, the display indicates a 32% apparent concentration when the actual concentration in the effluent is 13%. This result comes from a variety of factors. Such factors include size of the particular column, internal volume of the column, and the volume of tubes and connections leading into and out of the column.

It is possible to calibrate these columns, and important to do so in order to facilitate repeatable results. This can be done expediently by measurement of the effluent's refractive index and calculating actual ethanol concentration therefrom. In the following Table A, the calibration at 24° C. is shown for the "preparative column" and several flow rates of interest. These data do not specifically relate to fractions of the effluent that are of special interest. They merely illustrate the need for calibration and the calibration trends. The translation from refractive index to actual concentration of ethanol is based on measurement of 100% water, Sterile Water for Injection, U.S.P. (Cutter Labs, Berkeley, Calif.), 24° C., refractive index=1.3325; 100% ethanol, Punctilious Ethyl Alcohol, Dehydrated, 200 Proof, U.S.P. (U.S. Industrial Chemicals, Co., Tuscola, Ill.), 24° C., refractive index=1.3610. Each refractive index value shown in Table A is the mean of four measurements.

It should be noted that values for U.S.P. materials may differ from values for C.P. materials. However, U.S.P. materials should be used in these procedures, since the materials prepared are for human use. Further, it should be noted that the refractive index values shown here are based on use of a refractometer and ordinary light bulb, not Na light.

TABLE A

Calibration of Apparent & Actual Concentration of Ethanol (EtOH) for "Preparative Column" on Perkin-Elmer Series 3B HPLC Machine

| Elution time (min.) | 10 | 20 | 30 | 40 | 50 | 60 |
|---|---|---|---|---|---|---|
| Apparent Conc. EtOH (%) | 15–16.6 | 32–33.6 | 49.9–51.6 | 66.6–68.2 | 83.3–84.9 70 84.9 | 100 |
| 5.0 ml/min: | | | | | | |
| Refr. Index | 1.3324 | 1.3361 | 1.3462 | 1.3530 | 1.3585 | 1.3605 |
| Ac.Conc. EtOH (%) | 0 | 12.6 | 48.1 | 71.9 | 91.2 | 98.2 |
| 6.0 ml/min: | | | | | | |
| Refr. Index | 1.3327 | 1.3386 | 1.3483 | 1.3554 | 1.3603 | 1.3610 |
| Ac. Conc. EtOH (%) | 0.7 | 21.4 | 55.4 | 80.4 | 97.5 | 100.0 |
| 15 ml/min: | | | | | | |
| Refr. Index | 1.3370 | 1.3474 | 1.3575 | 1.3585 | 1.3605 | 1.3605 |
| Ac. Conc. EtDH (%) | 15.8 | 52.3 | 87.7 | 91.2 | 98.2 | 98.2 |

Furthermore, it is possible to calibrate actual percentage ethanol concentration against elution time, or tube number, for different flow rates, to facilitate the extraction procedure. If % EtOH is the Y-axis and elution time (or tube number) is the X-axis, a series of approximately S-shaped curves can be plotted. The 0.5 ml/min "analytic column" curve is that furthest to the right. To its left is the curve for 5 ml/min and the "preparative column." To the left of that is the curve for 6 ml/min and the same column, and so on. It is believed that the best results are realized by using refractive index, rather than elution time or tube number, as a measure of actual EtOH concentration, the latter being the factor directly related to the solubility and chemical structure of the materials of interest. Accordingly, refractive index data are used hereafter to identify the modulators in this specification and in the claims thereof. In referring to gradient composition, however, it was deemed more appropriate to describe the separation process in terms of v/v percentage composition, because that is the basis on which ethanol and water are mixed to form the gradient.

EXAMPLE 5

HPLC on Analytic Column

The material of Example 4 was purified and separated by HPLC on the analytic column, as described above, yielding 34 effluent fractions (30 plus 4 more at the end, after inputting pure ethanol, to fine tune the high concentration part of the gradient), which were each set aside.

Refractive index measurements were made on the effluent fractions at selected intervals in the process. The pertinent ethanol concentration data are tabulated below, in Table B.

TABLE B

| Tube No. | Elution Time (min.) | Apparent Conc. EtOH (Display) | Refr. Index (Meas.) | Actual Conc. EtOH (Calc.) |
|---|---|---|---|---|
| 5 | 10 | 15% | 1.3324 | 0 |
| 7 | 14 | 20% | 1.3326 | 0.4% |
| 14 | 28 | 45% | 1.3428 | 36% |
| 15 | 30 | 53% | 1.3440 | 40% |
| 21 | 42 | 70% | 1.3531 | 72% |
| 22 | 44 | 74% | 1.3543 | 76% |
| 24 | 48 | 80% | 1.3567 | 85% |
| 25 | 50 | 84% | 1.3580 | 89% |
| 27 | 54 | 89% | 1.3592 | 94% |
| 28 | 56 | 94% | 1.3596 | 95% |
| 29 | 58 | 96% | 1.3602 | 97% |
| 30 | 60 | 99% | 1.3606 | 99% |
| 33 | 66 | 100% | 1.3610 | 100% |
| 34 | 68 | 100% | 1.3620 | 100% |

EXAMPLE 6

Assay of Amplifier and S-Suppressor Fractions by DH Test

Figure 2:
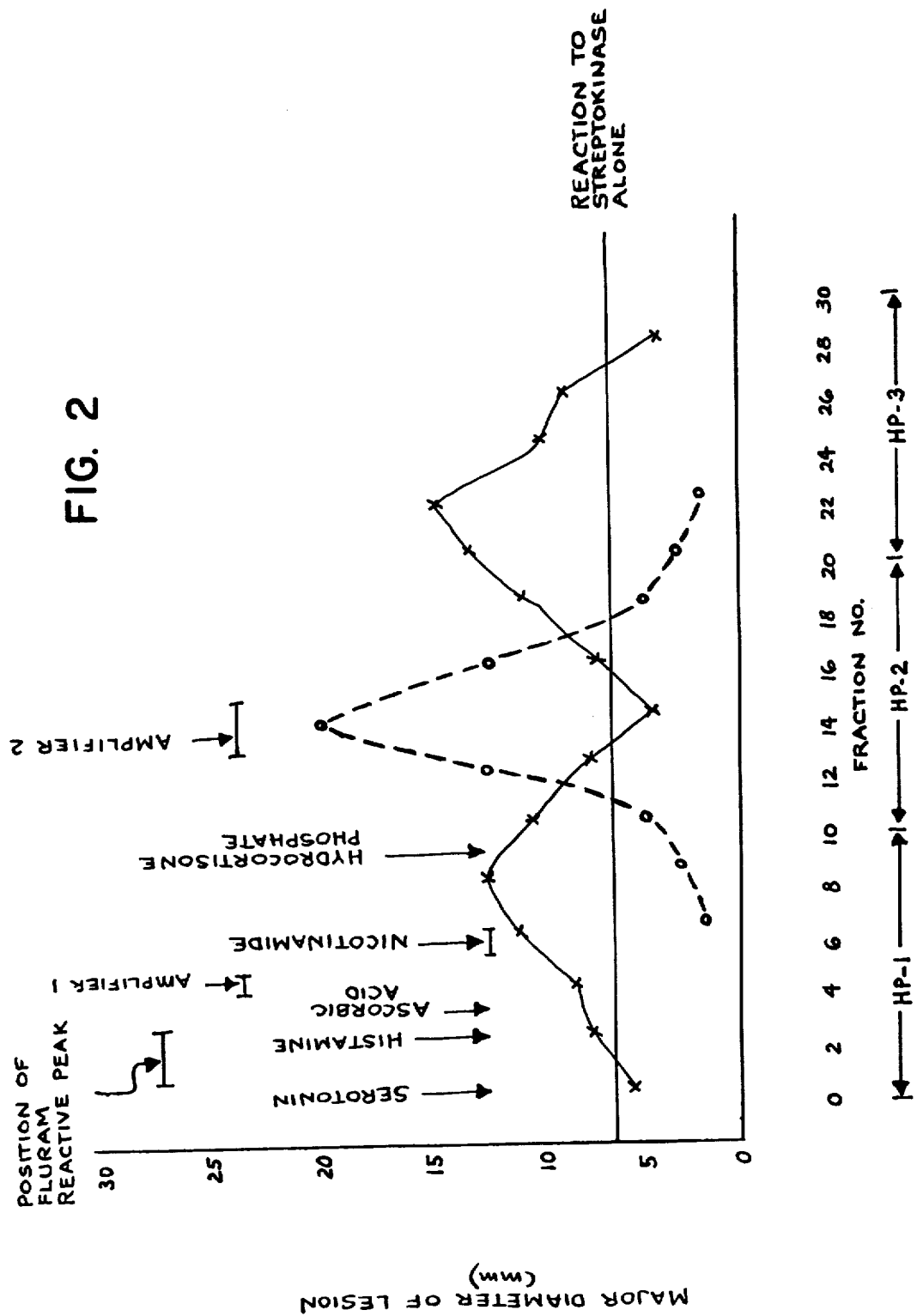
FIG. 2 is a graph of a human dermal response to fractions of leukocyte extract purified and separated by high pressure liquid chromatography on an analytic column; the dermal response is measured in terms of diameter of skin lesion caused by antigen.

The 30-plus fractions of Example 5 were lyophilized and redissolved in 0.5 ml normal saline. Individual odd-numbered fractions, 0.1 ml each, were injected intradermally in a recipient person, in combination with an antigen to which the recipient had been previously shown to be sensitive. The dermal responses at 24 hours were measured. The results are shown in FIG. 2.

In the separation shown in FIG. 2, the material was obtained from a donor person who was insensitive to the antigen streptokinase (hereinafter "SK"). The recipient person was known to be sensitive to streptokinase. The extent of his dermal reaction to SK in the absence of any modulators is presented as a horizontal line in FIG. 2. DH responses above the line show amplifier activity, while respones below the normal level suggest suppressor activity. For reference, also indicated in FIG. 2 are the positions of the fractions containing fluorescamine-reactive material and of various small molecules (serotinin, histamine, ascorbic acid, nicotinamide, and hydrocortisone phosphate) known to be vasoactive, inflammatory, or anti-inflammatory. The solid line of the graph shows the dermal reactivity of individual fractions in the concentrations obtained from the gradient.

EXAMPLE 7

Pool Assay, Diluted

The results of assays of individual fractions were compared with activity tests made with pooled fractions (0–10, 10–20, and 20–30) administered at several dilutions. Paradoxically, at higher dilution, the pooled 10–20 fractions manifested the maximum observed amplifier activity. The dilution effect of individual fraction 5, having maximal amplifier 1 activity, and fraction 14, were measured in a person sensitive to SK. The results were expressed by measurement in millimeters of the dimensions of the regions of erythema and of induration, at 7 hours, 12 hours and 24 hours after injection of antigen and modulator. The modulators were diluted in normal saline. These data are given in Table 1.

In the case of amplifier 1 (fraction 5 of FIG. 2), it is seen from Table 1 that strong acceleration of response and augmentation of response were observed at all tested levels of dilution, suggesting saturation of the test site at all concentrations studied. However, with fraction 14, it is seen from Table 1 that significant augmentation was observed only upon dilution by a factor of 10 to 1000. Therefore, a clear-cut optimum concentration for amplifier 2 activity was observed. A degree of acceleration of response was also observed, although less pronounced than than produced by amplifier 1.

The two apparent peaks of amplifier activity obtained by the measurement of undiluted samples in FIG. 2 do not necessarily reflect the true positions of the amplifiers in all preparations. There are several reasons for this. First, different donors have different levels of the various modulators in their leukocytes. They may also have other substances in their leukocytes that affect the preparation. There is also biological variability in the test recipient. Finally, there is the paradoxical effect of concentration in the case of amplifier 2. In particular, in FIG. 2, the decreased activity in the region of fractions 12 through 18 is clearly a consequence of above-optimal concentrations of amplifier 2 in this region. When optimally diluted, a peak of amplifier 2 activity should be observable in the region of fractions 14 through 16. This conclusion is represented by the dashed line in FIG. 2, which is a hypothetical curve of amplifier 2 activity measured at optimum dilution.

Figure 3:
FIG. 3 is a photograph of the arms of a patient, showing dermal response to antigen 24 hours after intradermal injection of various fractions of purified leukocyte extract.

Pooled fractions 21-30 had S-suppressor activity. When injected concurrently with antigen the S-suppressor effectively prevented the appearance of a DH response at 6 or 24 hours after injection. In contrast, a clear-cut DH response was observed at 24 hours where antigen was injected alone, and an even stronger response was observed where amplifiers 1 or 2 were also present. The results are shown in FIG. 3. The patient's left arm received a series of subcutaneous injections of PPD mixed with pooled fractions of the gradient shown in FIG. 2 at 1:10 and 1:100 dilutions, as indicated on the patient's arm: HP-1 (pooled fractions 1-10) designated HP-PK-1 on the patient's arm; HP-2 fractions 11-20) designated HP-PK-2; and HP-3 (fractions 21-30) designated HP-PK-3. The control injection of PPD alone was made on the patient's right arm. Increased inflammation, compared to control, is observable at the sites injected with pooled HP-1 and HP-2, due to the presence of amplifiers in these fractions. However, reduced inflammation is observed at HP-3 treated sites, due to the presence of suppressor activity, which appears to predominate over the activity of any amplifiers in this fraction. The S-suppressor activity was observed in pooled fractions 21-30 of the HPLC separation, in most donors. In some instances, S-suppressor activity could be found in single fractions, e.g., fraction 29 of FIG. 2. However, suppressor activity of single fractions was not considerably observed in all preparations and the presence of such activity proved to depend upon the donor individual.

When individual fractions in the region from 20 to 30 of the HPLC separation were assayed at several dilutions, the existence of amplifiers 3, 4, and 5 was discovered. The peak of amplifier 3 activity appeared in fractions 21 and 22, while amplifier 4 activity was centered in fraction 25, and amplifier 5 activity was found chiefly in fractions 27 and 28. S-suppressor was found in fractions 29 and 30. The results are shown in FIG. 4, showing analysis of a representative chromatographic run. In FIG. 4, DH response relative to controls was plotted as the extent of dermal reaction, defined as $(a \times b) - (a^* \times b^*)$, where a and b are diameters in millimeters of the erythematous lesion resulting from injection of fraction plus antigen, measured along mutually perpendicular axes, and $a^*$ and $b^*$ are the respective diameters of the control lesion resulting from injection of antigen alone. The extent of dermal reaction is therefore the difference between the approximate areas of lesions produced by antigen alone and antigen mixed with modulator. Values appreciably below the control level of zero, such as those observed in fractions 29 and 30, indicate suppressor activity, while values appreciably above zero indicate amplifier activity. It should be noted that the pattern in FIG. 4 is compatible with that of FIG. 2, when one considers the results of the odd-numbered fractions which were the only fractions assayed in the experiment shown in FIG. 2.

Amplifier 6 was eluted from the HPLC column after the ethanol-water gradient had reached an apparent concentration of 99.9% ethanol, by continuing the elution of the column with 100% ethanol at 0.5ml/min. collecting 1 ml fractions. Amplifier 6 was detected in tubes 32 through 34 under these conditions, with the greatest apparent concentration in tube 33.

Amplifier 6 caused an accelerated and augmented response to antigens to which the recipient was sensitive. A dose equivalent to the yield from $2 \times 10^8$ leukocytes in the described purification improved, and in some instances restored, the DH response of patients rendered weakly responsive by intercurrent illness, to antigens to which they were previously exposed. In general, the responses to amplifier 6 were enhanced by dilution, although the optimal dilution was variable with the individual recipient and perhaps depended upon the antigen as well. Table 4 shows the results of two dilution experiments. In part A, a streptokinase-sensitive recipient received 2.5 units of streptokinase simultaneously with the amplifier. 1.0 ml fractions of amplifier collected from the HPLC column was lyophilized and redissolved in 0.3 ml normal saline. 0.1 ml of the indicated fractions, diluted to the extent shown, with normal saline, was injected. In part B, a PPD-sensitive recipient was injected with 0.05 ml of a 1/10 dilution of standard Aplisol PPD, together with the dilution of amplifier 6 indicated, in 0.1 ml saline, or with 0.1 ml of normal saline alone as a control.

Material with amplifier activity is extractable from aqueous solution with ether. The extractable material requires dilution for maximal activity. The ether extract is therefore presumed to contain at least some of the described amplifiers. However, it is not known which of the described amplifiers are ether-extractable. Reverse-phase chromatographic separation of the above-described modulators can be carried out using a variety of known reverse-phase column materials known in the art. While conditions of elution may vary, the optimal conditions for separating the above-described modulators will be readily determined by those of ordinary skill in the art.

On the basis of the foregoing data, it is possible to characterize amplifiers 1-6 and S-suppressor more precisely. It is also possible to describe more precisely the procedures for purifying them and separating them from one another and from other materials.

Amplifiers 1-6 and S-suppressor are all characterized by (a) M.W. under 3500, and (b) being O.S. elutable with an ethanol-in-water gradient. (As used hereinafter, "O.S. elutable" with an ethanol-in-water gradient, means capable of being eluted from octadecyl silane by means of reverse-phase high pressure liquid chromatography with an ethanol-in-water gradient of increasing ethanol concentration.) The property of being O.S. elutable permits the further characterization and separation of these seven modulators because they can be ordered in terms of their relative solubility or elutability. Amplifier 1 is O.S. elutable in the portion of the gradient containing only 0–1% ethanol in the effluent. Amplifier 2 is O.S. elutable only in a greater concentration of ethanol, and so on, until Amplifier 6 is reached, which is O.S. elutable only in almost pure ethanol.

Each of these modulators can therefore be characterized in terms of four parameters;

(1) the given modulator is substantially entirely O.S. elutable in a specific zone of the gradient, from lower concentration limit a to upper concentration limit b;

(2) The modulator is substantially not O.S. elutable in the zone of the gradient below a;

(3) the modulator, when properly purified, is substantially free of material O.S. elutable in the zone below a; and (4) the modulator, when properly purified, is substantially free of material O.S. elutable only in the zone above b.

The third and fourth items may warrant further explanation. If an ethanol-in-water gradient is used that begins at a concentration in the middle or upper part of the range, e.g., 80%, then the first fraction that comes off will contain substantially all of the material O.S. elutable from 0 to 80%. Therefore, to properly purify material O.S. elutable from 80% to 88%, the gradient should begin below 80%, e.g., at 70% or 0%, so that all the material elutable in ethanol less concentrated than 80% will come off the column before the material elutable at 80% to 88% begins to come off. Otherwise, an ineffective purification will occur. This explains the presence of item (3) above.

The fourth item states a characteristic that should automatically occur in any procedure using a gradient of increasing concentration. If the gradient begins, e.g., at 80% or below, and stops at 88% or above, what elutes between 80% and 88% will be free of material O.S. elutable only at higher ethanol concentrations, such as 90%. This indicates, of course, that ethanol concentration in the gradient should always monotonically increase with time, in a proper purification procedure. That is the customary methodology.

The following table, Table C, characterizes these seven small M.W. modulators in terms of the four parameters discussed above. The data in Table C is essentially the same as that of Table B, above, presented in a different form. The horizontal lines of Table B separate the seven elution zones of interest with regard to these seven modulators. The basis of selection of the data tabulated in Table C was the result of dilution assays such as those of FIG. 4. That is, the seven zones were defined by the assays.

TABLE C

Elution Data for Amplifiers 1-6 and S-suppressor

| Modulator | Elution Time (min.) | Tube No. | Apparent Conc. EtOH (Display of P.E. Machine) | Refractive Index of Effluent (Measured) | Actual Conc. of EtOH (%) (Calculated) |
|---|---|---|---|---|---|
| Ampl-1 | 10–14 | 5–7 | 15–20 | 1.3324–1.3326 | 0–0.4 |
| Ampl-2 | 28–30 | 14–15 | 45–53 | 1.3428–1.3440 | 36–40 |
| Ampl-3 | 42–44 | 21–22 | 70–74 | 1.3531–1.3543 | 72–76 |
| Ampl-4 | 48–50 | 24–25 | 80–84 | 1.3567–1.3580 | 85–89 |
| Ampl-5 | 54–56 | 27–28 | 89–94 | 1.3592–1.3596 | 94–95 |
| S-Supp | 58–60 | 29–30 | 96–99 | 1.3602–1.3606 | 97–99 |
| Ampl-6 | 66–68 | 33–34 | 100 | 1.3610–1.3620 | 100 |

The foregoing descriptive and characterization data for the S-fraction modulators (amplifiers 1–6 and S-suppressor) can be summarized and explained as follows:

Amplifier 1

Amplifier 1 is characterized as having both an accelerating and augmenting effect on the DH skin response of recipients sensitive to a given antigen. The reactions produced by amplifier 1 administered with antigen reach peak intensity at about 6 to 14 hours after subcutaneous injection and fade rapidly thereafter. (In contrast, normal DH response, in the absence of amplifier, reaches a peak 24 to 30 hours after injection of antigen.)

Amplifier 1 is O.S. elutable between approximately 0 to 12% (v/v) ethanol concentration, that is, in the portion of the ethanol-in-water HPLC gradient where the effluent has a refractive index of from approximately 1.332 to 1.336. (The 1.336 refractive index figure and 12% concentration figure represent data from the use of the preparative column. Table C reflects only data from the use of the analytic column, which has shown a narrower elution range for amplifier 1.)

Amplifier 1 is not demonstrably reactive with fluorescamine, and is separated from the main peak of fluorescamine reactivity on HPLC. Amplifier 1 passes through a dialysis membrane having a nominal M.W. cutoff of 3500, so that the M.W. of amplifier 1 may be presumed to be less than 3500.

Amplifier 2

Amplifier 2 also causes both an accelerated and augmented response to antigen, although the degree of acceleration is somewhat less rapid than the response to amplifier 1. Reaction sites are more circumscribed than those produced by amplifier 1 plus antigen, and they persist considerably longer (up to seven days). Most suprisingly, maximal amplifying activity with amplifier 2 is observable only at an optimum concentration, with greater than optimal concentrations giving reduced amplification or even suppression of the DH response.

Amplifier 2 is O.S. elutable in the portions of the foregoing ethanol-in-water gradient between approximately 28 to 50% where the refractive index of the effluent is from approximately 1.340 to 1.347. Otherwise, amplifier 2 has the properties of amplifier 1 described above. In addition, it has been observed that amplifier 2 is stable to heating for 30 minutes at 56° C., but loses its activity if heated for 30 minutes at 90° C. (as in the case of amplifier 1, the immediately preceding concentration and refractive index data reflect data from the use of the preparative column, while Table C reflects data from the analytic column, which has a narrower elution range for amplifier 2.)

Amplifiers 3–6

Amplifiers 3, 4, 5, and 6 cause augmented response to antigen. Dilution studies indicate that the activity of amplifiers 3, 5, and 6 is enhanced by dilution. The activity of amplifier 4 may also be so enhanced, but the data is more equivocal. Amplifier 6 has been shown to have systemic effects. Otherwise, amplifiers 3 to 6 have substantially the properties of amplifier 1 described above. Amplifiers 3 to 6 are O.S. elutable in the approximate portions of the gradient indicated below in Table D. Data for amplifiers 1 and 2 are also restated for comparison.

TABLE D
Ethanol Concentration Data for Amplifiers

| Amplifier | Ethanol concentration | Refractive index |
|---|---|---|
| 1 | 0 to 12% (v/v) | 1.332 to 1.336 |
| 2 | 28 to 50 | 1.340 to 1.347 |
| 3 | 65 to 80 | 1.353 to 1.355 |
| 4 | 81 to 91 | 1.356 to 1.358 |
| 5 | 92 to 97 | 1.359 to 1.360 |
| 6 | 99 to 100 | 1.361 to 1.362 |

S-Suppressor

S-suppressor is characterized as having a temporary suppressing effect on DH response to the reintroduction of an antigen that previously challenged the subject. The effect lasts about 48 hours, after which DH response returns. S-suppressor has this suppressing effect when administered before or substantially concurrently with the antigen, but not when administered six hours or more after the antigen.

S-suppressor also is capable of affecting the phenomenon of leukocyte migration inhibition. Ordinarily, when leukocytes from a sensitive individual are exposed to an antigen to which the individual is sensitive, the leukocytes lose their ability to migrate in a fluid or semi-solid medium. This phenomenon of leukocyte migration inhibition is reversed by S-suppressor, if S-suppressor is present at an optimal concentration. In effect, S-suppressor inhibits the phenomenon of leukocyte migration inhibition permitting the leukocytes to migrate normally. The phenomenon of leukocyte migration inhibition in the presence of antigen is known to be correlated with a state of delayed hypersensitivity to that antigen. The reversal of leukocyte migration inhibition by S-suppressor is therefore believed by the inventor to be correlated with S-suppressor's suppression of a DH response.

S-suppressor is isolated from the dialysate passing through a membrane having a nominal 3500 M.W. cutoff, so that it too may be presumed to have M.W. less than 3500. S-suppressor is identifiable and separable from amplifiers 1 to 6 by HPLC. S-suppressor is O.S. elutable in fractions eluting from approximately 97% to 99% ethanol, where the refractive index of the effluent is from approximately 1.3600 to approximately 1.3608.

S-suppressor is not demonstrably reactive with fluorescamine, as judged by its separability from the major fluorescamine-reactive peak on HPLC. Suppression of a DH skin reaction is manifested when S-suppressor is injected before or concurrently with a test antigen to which the recipient gives a DH response. Suppression is reversible or short-acting, in effect delaying the onset of the DH response about 72 hours. Suppression is not observed when amplifier 2 is injected concurrently with S-suppressor.

L-Suppressor

An eighth modulator, designated herein as "L-suppressor," is found in that fraction of the leukocyte extract passing through a dialysis membrane having a nominal 12,000 M.W. cutoff, but retained by membrane having a 3500 M.W. cutoff, so that M.W. may be presumed to be greater than 3500 and less than approximately 12,000. L-suppressor activity is reversible, like that of S-suppressor, having a suppressing effect lasting about 72 hours. L-suppressor is not fluorescamine-reactive, as judged by the fact that it is separable from the major fluorescamine-reactive peak, upon hydroxylapatite chromatography. The following Examples 8 and 9 exemplify the purification procedure for preparing L-suppressor.

EXAMPLE 8

Fractionation of the L Dialysis Fraction

The "L" dialysis fraction of Example 2 (or Example 3, which is an equivalent of Example 2) was further fractionated by chromatography on hydroxylapatite. After removal of fines, hydroxylapatite previously equilibrated with 5 mM ammonium bicarbonate was packed in a 1.5×20 cm column. The L fraction, lyophilized and redissolved in 0.05M ammonium bicarbonate, was applied to the column. The column was eluted with a gradient of 0.05M to 0.2M aqueous ammonium bicarbonate (115 ml), followed by a gradient of 0.2M to 0.6M ammonium bicarbonate (65 ml). 1 ml fractions were collected and set aside.

EXAMPLE 9

Assay of L Fraction

The 1 ml fractions of Example 8 were monitored for absorbance at 260 nm and reactivities with fluorescamine. Individual fractions were pooled in seven combined fractions spanning most of the gradient. The combined fractions were analyzed for biological activity by injecting each fraction intradermally in the presence of an antigen to which the recipient individual was sensitive. The results are shown in Table 2. Relative DH response is indicated in Table 2 by the diameter of the region of induration, in millimeters, measured at 25 and 43 hours, compared to a control-reaction site wherein antigen alone was injected.

Fractions 450 and 451, eluting between 0.1M and 0.15M ammonium bicarbonate were those of interest. They strongly suppressed the DH reaction for at least 43 hours. At 72 hours, reactions measuring 10 mm × 10 mm were seen at sites receiving fractions 450 and 451, indicating that the suppressor activity is temporary and reversible over time.

It was believed desirable to use controls to test the validity of the foregoing data. Several such experiments are described below.

Red Cell Control

Dialyzed red blood cell extracts were prepared in the same fashion that leukocyte extracts were prepared in Example 2. Differential dialysis and column chromatography on Sephadex G-10 were performed as described above. No immune modulator activity was observed in the resulting fractions. Therefore, it was concluded that the observed biological activity was not introduced by the extraction and purification steps. In addition, extracts of platelets subjected to identical purification steps, were devoid of modulator activity. Some of the purified amplifiers have been re-chromatographed and found to behave in essentially the manner observed during initial purification.

Transfer Factor Control

In view of the significant body of prior art dealing with transfer factor, it was important to show, as unequivocally as possible, that the observed amplifications of recipient sensitivity were not in fact due to the transfer of a low-level sensitivity, previously undetected in the donor, which, when concentrated, would appear as amplified sensitivity in a recipient. The experimental strategy used herein was based upon testing for antigens having geographically localized prevalence or having a medically traceable source.

PPD, a purified protein derivative of tubercle bacillus, is both medically traceable and geographically localized. Sensitivity to PPD occurs in individuals with a prior history of vaccination with BCG (Bacille Calmette-Guerin), widely used to immunize against tuberculosis in Europe. However, its use has not been approved in the United States.

Histoplasmin is a geographically-localized antigen. Sensitivity to histoplasmin is widespread in the southern United States and in tropical regions, where histoplasmosis is endemic. But sensitivity to histoplasmin is not found in northern Europe, where histoplasmin does not occur.

In the control experiment, the donor, a native of the southeastern United States, was skin-test sensitive to histoplasmin, but was non-reactive to PPD. The recipients were lifetime residents of the United Kingdom with either a demonstrable skin test sensitivity to PPD or prior history of vaccination with BCG. The amplifier preparation employed in this experiment was purified as described, through the Sephadex G-10 fractionation step, except that a shorter, 80 cm column with somewhat lower resolution was employed. Consequently, test material was a mixture of amplifiers 1–6 and S-suppressor, in addition to fluorescamine-reactive material. The results are nevertheless significant as proof of the lack of transfer factor activity in the preparation.

The results are shown in Table 3. Two recipients were each tested with two fluorescamine-reactive peak fractions (number 33 and 34 of the Sephadex column). Each fraction, 2.4 mg based upon fluorescamine reactivity, was injected either alone or with 25 units of PPD. Fourteen hours after the initial injection, the sites which had not previously received antigen were challenged with histoplasmin, using 0.1 ml of Histoplasmin Antigen (preparation of Parke-Davis Corp., Detroit, Mich., sold as 1/100 (W/V) dilution in normal saline). Control sites, with PPD or histoplasmin injected alone, at the appropriate time, were also prepared.

In Table 3, the intensity of the dermal skin reaction is expressed in terms of the diameter in mm of the zone of induration surrounding the injection site. The data show that the recipients lacked any capacity to react with histoplasmin, either before or after injection of leukocyte extract fractions. Both the accelerating and augmenting aspects of amplifier activity are observable. On the other hand, no transfer of histoplasmin sensitivity is observable.

Systemic Effect Experiment (Sarcoidosis)

An important aspect of the amplifier activities described herein is their systemic effectiveness. Furthermore, their systemic effects can be observed in anergic patients (those who have lost their normal immune responsiveness due to illness). Patients with a history of BCG vaccination and who were currently non-responsive to PPD as a result of illness could be rendered responsive to PPD by a subcutaneous injection of the amplifier fraction described in Example 2B, supra, using a 10- to 100-fold higher dose of the amplifier. Response to the antigen was not localized to the site of amplifier injection.

Systemic effects were also dramatically demonstrated in a series of experiments using amplifier 6. A patient with a four-year history of sarcoidosis displayed extremely weak responses to all antigens. The following series of tests was performed. On day 1 of the tests, the patient was administered tetanus toxoid, alone and in combination with amplifier 6 at several dilutions. The results, shown in Table 5, showed a weak erythematous response without induration to tetanus toxoid alone, and some slight amplification of response with amplifier 6. However, there was no induration at any of the test sites, indicating that the patient was not responding appropriately. On day 2 of the test, the patient received a subcutaneous injection of amplifier 6 from fraction 33 of the reverse-phase chromatography, in an amount equivalent to that extractable from approximately $2 \times 10^8$ leukocytes. On day 8 of the test, the patient was again challenged with tetanus toxoid, alone and in combination with several dilutions of amplifier 6, as before. However, this time there was a substantial response to amplifier 6, with some induration noted, as shown in Table 5. The results indicate a substantially increased responsiveness to the antigen, modulated by a systemic effect of the injection of amplifier 6 administered on day 2.

Systemic Effect Experiment (Lymphocyte Activation)

Further evidence of the systemic effect of amplifier 6 is provided by measurement of responsiveness of the patient's peripheral blood lymphocytes to activation in vitro. Lymphocyte activation is a well-known phenomenon. A sample of peripheral blood lymphocytes of normal individuals is induced to proliferate in cell culture by a variety of known activating agents, including various plant mitogens and phytohemagglutinin (hereinafter PHA). The rate of proliferation is manifested by uptake of $^3$H-thymidine from the culture medium into DNA of the dividing cells. The test procedure is described by Oppenheim, J. J., et al., in *In Vitro Methods of Cell Mediated and Tumor Immunity* (Bloom and David, eds.), pp. 573–585, Academic Press, New York, N.Y. (1976).

Samples of peripheral lymphocytes were obtained from the patient on day 2 and day 8 of the above-described test, and assayed for response to a variety of activating agents. The results are shown in Table 6. Day 2 lymphocytes were well below the normal response level, while day 8 lymphocytes displayed normal or increased responsiveness to two of the three activators. Therefore, a substantial systemic response to the subcutaneous injection of amplifier 6 had occurred.

In the foregoing experiments, pokeweed mitogen was obtained from Gibco Laboratores, Grand Island, N.Y.; PHA and concanavalin A were obtained from Difco Laboratories, Detroit, Mich. The results in Table 6 are expressed as counts per minute of $^3$H-thymidine uptake.

On the basis of experimental results on individual volunteers, it is believed that recipients having non-genetic anergic or hypoimmune conditions can be treated to increase immune responsiveness by the above-described amplifiers. Some of the experimental results on volunteers were obtained using material purified by Sephadex G-10 chromatography, presumably comprising a mixture of amplifiers. A preferred embodiment of the contemplated method of treatment is described as follows.

EXAMPLE 10

Increase of Immune Response

Amplifiers 1-6 are prepared and purified as described in Example 1-5, using HPLC. Active fractions are pooled, lyophilized, and redissolved in normal saline or other physiologically acceptable vehicle. An effective dose, e.g., 0.1 ml containing the equivalent amount of amplifiers 1-6 purified from $5 \times 10^7$ leukocytes, is injected subcutaneously. Increased immune responsiveness is monitored by the patient's reactivity to an antigen to which he is known to be sensitive, comparing reactivity before and after administering the amplifiers. The amplifiers are administered either individually, or in combination, depending upon the desired effects. The persistence of the systemic modulation produced by administration of the amplifiers varies from patient to patient, and must therefore be monitored periodically with a suitable sensitivity test, as described. Additional doses are administered as required to maintain a desired amplification of immunity based upon the professional judgment of the attending physician.

The amplifiers, either singly or in combination, can be used to produce an immune response to weak vaccines. Many pathogens, including several Staphylococcus varieties and fungi responsible for Histoplasmosis or Candidiasis, fail to provoke a strong immune response in certain patients. Moreover, there is no known satisfactory vaccine for conferring immunity on such patients. Such fungal infections are especially dangerous for patients subjected to cancer chemotheraphy, or immunosuppressive drugs. By enhancing the patients' immune response to weak antigens, however, the concurrent administration of the described amplifiers, either singly or in combination, makes it possible to prepare vaccines against such pathogens. Patients about to receive chemotherapy, or transplant surgery, can thus be vaccinated prior to treatment to reduce their susceptibility to histoplasmosis or candidiasis. Used as described below, amplifiers 1-6 are expected to expand the scope of preventative measures in medicine, and to enlarge the range of weak antigens which can be used for immunization.

EXAMPLE 11

Vaccination

Vaccine is preferably prepared by combining amplifiers 1-6 with antigens of the desired pathogen, prepared according to known methods in the art to ensure adequate attenuation and sterility. The vaccine is then administered by standard procedures.

Severe skin reactions to poison ivy or other contact hypersensitivity reactions are preventable by treatment with S-suppressor. Such a treatment would proceed on the basis of the known fact that the major portion of contact dermatitis reactions, such as that of poison ivy or other allergens, is a DH reaction.

EXAMPLE 12

Suppression of Contact Dermatitis

S-suppressor is purified and incorporated into a salve or ointment suitable for topical application, such as a cold-cream-base composition.

Since the yield of observed suppressor activity obtained from individual donors is variable, the applied dosage must be expressed in terms of activity units. One suppressor unit may be defined as the minimum amount necessary to reduce the diameter of induration in an individual's DH response, by 5 mm. Using this definition, the skin area of the patient to be treated should receive a dose of at least one suppressor unit per 100 cm$^2$, which is an effective doseage amount, with larger doses being administered if clinically indicated. Treatment should be continued as long as there is danger of exposure, with reapplications at least every seven days, but more frequently if clinically indicated. The response of individual patients will vary depending upon their degree of sensitivity to the antigen, and their responsiveness to suppressor. Such compositions may also advantageously include steroids or other anti-inflammatory agents to enhance their therapeutic effect.

EXAMPLE 13

Prevention of Contact Dermatitis

Severe poison ivy and other contact skin reactions are preventable by the administration of L-suppressor. Again, the known DH component of such skin reactions indicates the effectiveness of such a therapeutic approach. Active fractions from hydroxylapatite chromatography should be pooled, lyophilized, and incorporated into a salve or ointment composition suitable for topical application. Where the reaction is generalized, parenteral administration may be preferred. Dosage and method of treatment follow essentially as described in the preceding example.

The L-suppressor material and S-suppressor material may be applied separately, or mixed together in a single composition.

GENERAL CONCLUDING REMARKS

The above described modulators of the immune system are considered to be materials whose natural function is regulation of the immune response, directly with respect to cell mediated immunity and perhaps indirectly affecting humoral immunity as well. The materials have been prepared with a high degree of purity such that their properties have now been characterized and shown to be entirely and unexpectedly different from transfer factor and from partial fractionations thereof reported in the prior art. It will be understood, however, that the materials disclosed and claimed herein are defined in terms of their biological activities and physical properties and do not necessarily consist of single molecules or chemical entities.

The amplifier and suppressor materials herein described are medically useful for the treatment of patients suffering from a variety of hyperimmune and hypoimmune conditions. It is especially significant that these materials may be isolated from normal individuals, rather than from specific identified donors, so that large-scale purification from pooled sources is feasible.

On the basis of the preceding data and discussion, it is now also possible to define and to characterize more precisely some of the terms used herein.

Modulators

The terms "modulator" and "modulator material" are generically applied to all of the biologically active materials of this invention. They are derived from leukocytes. They are in purified form, and in particular are purified substantially free of fluorescamine-reactive substances. They affect a response, whether direct or indirect, of the immunity system of an animal or human body, portion of said body, or matter taken from said body. The response is to the reintroduction of antigens to which the animal or human body was previously exposed; the response occurs upon or following the reintroduction of such an antigen; the response is specifically attributable to a function of the immunity system.

As used herein, generally, "modulator material" is collective and has several different components, each component being termed a "modulator." The given modulator or specimen of modulator material used for any biological purpose is substantially free of other material, such as a second modulator, that has an opposite effect to the effect of the given modulator on the immune system. That is, modulator material is a generic term for material containing amplifiers, or suppressors, or other modulators. This can include a mixture of amplifiers or a mixture of suppressors. But the term is not used to refer to a mixture in which both amplifier material and suppressor material are present at the same time, as such a mixture would contain mutually antagonistic or nullifying ingredients. Usually the term "modulator" is applied to a particular, even though not specifically designated, species (member of the genus) of modulator, such as amplifier 3 or L-suppressor.

Human Modulators

There is a major subgenus of modulators, "human modulators." In "human modulator material," the leukocytes from which the material is derived are human leukocytes, and the kind of immune response of a body that the modulator material affects is that of a human body. A "human modulator" is an individual substance present in human modulator material.

The human modulators of principal interest herein are those modulators that increase or decrease the speed or magnitude of immune response. This principal subgenus does not include those modulators, referred to but not described herein, that primarily modulate other aspects of immunity response, such as duration of response, threshold of sensitivity, and type of response (e.g., proliferation of lymphocytes).

Amplifiers

"Amplifier material" is human modulator material that increases the speed (accelerates onset) of or increases the magnitude (augments) the immune response, or does both. Amplifier material includes at least six specific amplifiers. The six disclosed herein are designated by the numbers 1 to 6. These are all S-fraction (M.W. under 3500) and O.S. elutable modulators. Other amplifiers may hereafter be extracted by extrapolation from the teachings of this disclosure.

The six claimed amplifier species designated by the numbers 1-6 are all characterized by the four parameters referred to previously, in terms of the respective zones in which they are O.S. elutable, and below which they are not O.S. elutable, as well as their purification from the freedom from materials O.S. elutable outside that zone. The six approximate zones are tabulated above in Table D. The same zones of Table D are used in the claims hereinbelow.

Suppressors

"Suppressor material" is human modulator material that decreases the speed of onset of or decreases the magnitude of an immune response. A suppressor is a particular kind of such material. The invention includes two specific suppressors, S-suppressor and L-suppressor. S-suppressor is an S-fraction material, characterized in terms of the same parameters as amplifiers 1-6. L-suppressor is characterized in terms of its 3500-12,000 M.W. and its elutability characteristics.

The invention is also considered to include the novel processes for purification and extraction of these new materials, described herein, as well as the novel compositions including these materials and the methods using them, disclosed herein.

While the invention has been described in connection with specific and preferred embodiments thereof, it will be understood that it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains. For example, as the terms "dialysis" and "dialyzed through a dialysis membrane" are used herein, they should be understood to include equivalent methods of separating molecules and/or biological "activities" of different sizes and/or weights. Thus, "dialysis" as used herein includes ultrafiltration, ultracentrifugation, and electrophoresis. As another example, "gel filtration" includes gel exclusion chromatography on a high performance liquid chromatographic system.

TABLE 1

| | DILUTION STUDIES OF FRACTIONS 14 AND 5 FROM REVERSE-PHASE CHROMATOGRAPHY | | | | | |
|---|---|---|---|---|---|---|
| | 7 Hours | | 12 Hours | | 24 Hours | |
| Fraction #14 | Erythema | Induration | Erythema | Induration | Erythema | Induration |
| Undil. + SK | 12 × 11 | 0 | 14 × 18 | 0 | 11 × 11 | 0 |
| $10^{-1}$ + SK | 18 × 16 | 18 × 16 | 26 × 25 | 15 × 15 | 20 × 20 | 0 |
| $10^{-2}$ + SK | 15 × 13 | 15 × 13 | 23 × 23 | 15 × 15 | 10 × 11 | 10 × 11 |
| $10^{-3}$ + SK | 15 × 20 | 15 × 20 | 21 × 23 | 12 × 12 | 18 × 14 | 18 × 14 |
| $10^{-4}$ + SK | 0 | 0 | 4 × 3 | 0 | 9 × 9 | 4 × 4 |
| SK Control | 0 | 0 | 15 × 15 | 6 × 6 | 9 × 11 | 9 × 11 |
| | 7 Hours | | 12 Hours | | 24 Hours | |

TABLE 1-continued

DILUTION STUDIES OF FRACTIONS 14 AND 5
FROM REVERSE-PHASE CHROMATOGRAPHY

| Fraction #5 | Erythema | Induration | Erythema | Induration | Erythema | Induration |
|---|---|---|---|---|---|---|
| Undil. + SK | 20 × 20 | 20 × 20 | 25 × 30 | 20 × 20 | 15 × 20 | 15 × 20 |
| $10^{-1}$ + SK | 20 × 15 | 20 × 15 | 26 × 20 | 12 × 12 | 12 × 14 | 12 × 14 |
| $10^{-2}$ + SK | 18 × 18 | 18 × 18 | 23 × 22 | 20 × 20 | 15 × 18 | 15 × 18 |
| $10^{-3}$ + SK | 16 × 18 | 16 × 18 | 21 × 21 | 20 × 20 | 13 × 12 | 13 × 12 |
| $10^{-4}$ + SK | 20 × 20 | 20 × 20 | 25 × 25 | 25 × 24 | 26 × 24 | 26 × 24 |
| SK Control | 0 | 0 | 2 × 3 | 0 | 7 × 6 | 4 × 4 |

SK = streptokinase

TABLE 2

"L" Fraction from Hydroxylapatite

| Fraction | 25 Hours Induration (mm) | 43 Hours Induration (mm) |
|---|---|---|
| 448 | 14 × 17 | 14 × 14 |
| 449 | 25 × 25 | 20 × 18 |
| 450 | 3 × 3 | 3 × 3 |
| 451 | 3 × 2 | 3 × 4 |
| 452 | 16 × 16 | 15 × 14 |
| 453 | 12 × 16 | 18 × 17 |
| 454 | 14 × 10 | 15 × 14 |
| Control PPD (2.5 units) | 26 × 24 | 26 × 13 |

TABLE 3

Donor: TK
Recipient: SS

| Fraction No. | 2 hr. | 4 hr. | 8 hr. | 24 hr. | | 48 hr. |
|---|---|---|---|---|---|---|
| 33 | | | | 5 | Histo | 0 |
| 34 | | | | 0 | Histo | 0 |
| 33 + PPD | | | | 25 | | 30 |
| 34 + PPD | | | | 35 | | 50 |
| PPD | | | | 8 | | 30 |
| | | | | | Histo | 0 |

Donor: TK
Recipient: SJ

| Fraction No. | 2 hr. | 4 hr. | 8 hr. | 24 hr. | | 48 hr. |
|---|---|---|---|---|---|---|
| 33 | 8 | 7 | 8 | 8 | Histo | 0 |
| 34 | 0 | 0 | 0 | 0 | Histo | 0 |
| 33 + PPD | 7 | 7 | 20 | 20 | | 30 |
| 34 + PPD | 0 | 5 | 3 | 35 | | 50 |
| PPD | 0 | 0 | 0 | 25 | | 20 |
| | | | | | Histo | |

TABLE 4

A. EXTENT OF DERMAL REACTION AT INDICATED TIME*

| Fraction | 5.5 hrs. | 12.5 hrs. | 24 hrs. |
|---|---|---|---|
| 32 | 96 | 36 | 15 |
| 32 ($10^{-2}$ dilution) | 120 | 360 | 173 |
| 35 | 90 | 156 | −14 |
| 35 ($10^{-2}$ dilution) | 132 | 428 | 129 |
| 37 | 36 | 75 | −7 |
| 37 ($10^{-2}$ dilution) | 132 | 356 | 159 |

B. EXTENT OF DERMAL REACTION AT INDICATED TIME*

| Fraction | 4 hrs. | 11 hrs. |
|---|---|---|
| 33 ($10^{-1}$ dilution) | 8 | 41 |
| 33 ($10^{-2}$ dilution) | 41 | 48 |
| 33 ($10^{-3}$ dilution) | 99 | 255 |
| 33 ($10^{-4}$ dilution) | 89 | 167 |

*(a × b) − (a* × b*) in mm²

TABLE 5

| | Lesion Dimensions in Millimeters | | |
|---|---|---|---|
| A. DAY 1 RESPONSE | 10.5 hrs | 23 hrs. | 45 hrs. |
| Tetanus Toxoid (TT) | 15 × 20 | 10 × 10 | 15 × 15 |

TABLE 5-continued

| | | | |
|---|---|---|---|
| TT + Amplifier 6 ($10^{-1}$ dilution) | 20 × 25 | 14 × 12 | 20 × 25 |
| TT + Amplifier 6 ($10^{-2}$ dilution) | 20 × 20 | 14 × 10 | 20 × 20 |
| TT + Amplifier 6 ($10^{-3}$ dilution) | 10 × 10 | 10 × 11 | 15 × 15 |
| TT + Amplifier 6 ($5 \times 10^{-3}$ dilution) | 15 × 20 | 7 × 7 | 10 × 10 |

| | Lesion Dimensions in Millimeters | |
|---|---|---|
| B. DAY 8 RESPONSE | 8 hrs. | 20 hrs. |
| TT (control) | 10 × 15 | 10 × 10 |
| TT + Amplifier 6 ($10^{-1}$ dilution) | 40 × 36 | confluent 10 × 18 |
| TT + Amplifier 6 ($10^{-2}$ dilution) | 15 × 18 | |
| TT + Amplifier 6 ($10^{-3}$ dilution) | 15 × 15 | 10 × 15 + Amplifier 6  15 × 15 |
| TT + Amplifier 6 ($5 \times 10^{-3}$ dilution) | | |

TABLE 6

LYMPHOCYTE ACTIVATION

| | hu 3H-thymidine uptake, cpm | | |
|---|---|---|---|
| Activator | Patient/Day 2 | Normal | Patient/Day 8 |
| None (media control) | 419.0 | | 530.0 |
| Pokeweed Mitogen | 8,001.7 | >20,000 | 17,279.9 |
| Concanavalin A | 9,173.1 | >20,000 | 34,066.3 |
| PHA-P 1:50 | 20,208.3 | >40,000 | 27,899.2 |
| PHA-P 1:200 | 6,605.1 | | 7,257.1 |
| PHA-P 1:800 | 551.1 | | 1,710.3 |

The following is the claimed subject matter:

1. A process of purifying modulator material from an extract of human leukocytes, and of separating said material from substantially all fluorescamine-reactive material and from L-suppressor, comprising the steps of:

(1) dialyzing said extract through a dialysis membrane having a nominal molecular weight cutoff of about 3500, thereby producing a dialysate;

(2) fractionating said dialysate by gel filtration, thereby producing a plurality of dialysate-fractions;

(3) modulator-assaying said dialysate-fractions, thereby ascertaining modulator activity of said dialysate-fractions;

(4) selecting modulator-assayed dialysate-fractions having substantial modulator activity and pooling them;

(5) applying said selected and pooled modulator-assayed dialysate-fractions to a reverse-phase high pressure liquid chromatography column, packed with octadecyl silane, (6) eluting said column with an ethanol-in water gradient, thereby producing a plurality of effluent-fractions; and (7) selecting predetermined effluent-fractions on the basis of ethanol concentration therein, and collecting them.

2. The process of claim 1 wherein:
(a) said gradient includes ethanol in water from a concentration of approximately 0% to at least approximately 12%, and
(b) said selected and collected effluent-fractions are those having a refractive index between approximately 1.332 and approximately 1.336, whereby a first amplifier is extracted in substantially purified form.

3. The process of claim 1 wherein:
(a) said gradient includes ethanol in water from below approximately 28% to at least approximately 50%, and
(b) said selected and collected effluent-fractions are those having a refractive index between approximately 1.340 and approximately 1.347, whereby a second amplifier is extracted in substantially purified form.

4. The process of claim 1 wherein:
(a) said gradient includes ethanol in water from below approximately 65% to at least approximately 80%, and
(b) said selected and collected effluent-fractions are those having a refractive index between approximately 1.353 and approximately 1.355, whereby a third amplifier is extracted in substantially purified form.

5. The process of claim 1 wherein:
(a) said gradient includes ethanol in water from below approximately 81% to at least approximately 91%, and
(b) said selected and collected effluent-fractions are those having a refractive index between approximately 1.356 and approximately 1.358, whereby a fourth amplifier is extracted in substantially purified form.

6. The process of claim 1 wherein:
(a) said gradient includes ethanol in water from below approximately 92% to at least approximately 97%, and
(b) said selected and collected effluent-fractions are those having a refractive index between approximately 1.3590 and approximately 1.3598, whereby a fifth amplifier is extracted in substantially purified form.

7. The process of claim 1 wherein:
(a) said gradient includes ethanol in water from below approximately 97% to at least approximately 99%, and
(b) said selected and collected effluent-fractions are those having a refractive index between approximately 1.3600 and approximately 1.3608, whereby a first suppressor is extracted in substantially purified form.

8. The process of claim 1 wherein:
(a) said gradient includes ethanol in water from below approximately 98% to and including pure ethanol, and
(b) said selected and collected effluent-fractions are those having a refractive index over approximately 1.3608, whereby a sixth amplifier is extracted in substantially purified form.

9. A process of purifying L-suppressor material from an extract of human leukocytes, and of separating said L-suppressor material from amplifiers 1–6, from S-suppressor, and from substantially all fluorescamine-reactive material, comprising the steps of:

(1) dialyzing said extract through a first dialysis membrane having a nominal molecular weight cutoff of approximately 12,000, thereby producing a first dialysate,
(2) dialyzing said first dialysate through a second dialysis membrane having a nominal molecular weight cutoff of about 3500, thereby producing a second dialysate and a retentate of the second dialysis,
(3) applying said retentate of the second dialysis to a hydroxylapatite chromatography column,
(4) eluting said column with ammonium bicarbonate aqueous solution gradient from approximately 0.08M to approximately 0.2M, and
(5) collecting the material eluting between approximately 0.1M and 0.15M.

10. The product of the process of claim 1.
11. The product of the process of claim 2.
12. The product of the process of claim 3.
13. The product of the process of claim 4.
14. The product of the process of claim 5.
15. The product of the process of claim 6.
16. The product of the process of claim 7.
17. The product of the process of claim 8.
18. The product of the process of claim 9.

19. A composition of matter consisting of material which:
(a) is derived from leukocytes;
(b) is in purified form, and is purified substantially free of fluorescamine-reactive substances;
(c) affects a response of the immunity system of an animal or human body, portion of said body, or matter taken therefrom, where said response:
(1) is to the reintroduction to said body of at least one antigen to which said body has been previously exposed,
(2) is specifically attributable to a function of the immunity system of said animal or human, and
(3) occurs following said reintroduction of said antigen; and
(d) is substantially free of other, different material that has an effect on said response opposite to the effect to the effect of said composition on said response— said composition of matter being hereinafter referred to as "modulator material."

20. Modulator material of claim 19 with the further limitation that:
(a) said luekocytes from which said modulator is derived are human leukocytes; and
(b) said body is a human body— said further-limited modulator material being hereinafter referred to as "human modulator material."

21. Human modulator material of claim 20 with the further limitation that said modulator affects said resuponse by increasing the speed or magnitude of said response—said further-limited human modulator material being hereinafter referred to as "amplifier material."

22. Amplifier material of claim 21 with the further limitation that said amplifier material is:

(a) dialyzable through a dialysis membrane having a nominal molecular weight cutoff of about 3500; and (b) O.S. elutable with an ethanol-in-water gradient.

23. Amplifier material of claim 22, further limited by being material substantially:
   (a) entirely O.S. elutable in the portions of said gradient where the effluent has a refractive index between approximately 1.332 and approximately 1.336;
   (b) not O.S. elutable in the portions of said gradient where the effluent has a refractive index under approximately 1.332;
   (c) free from material O.S. elutable in the portions of said gradient where the effluent has a refractive index under approximately 1.332; and
   (d) free from material O.S. elutable only in the portions of said gradient where the effluent has a refractive index over approximately 1.336—
said further limited amplifier material being hereinafter referred to as "amplifier 1."

24. Amplifier material of claim 22, further limited by being material substantially:
   (a) entirely O.S. elutable in the portions of said gradient where the effluent has a refractive index between approximately 1.340 and approximately 1.347;
   (b) not O.S. elutable in the portions of said gradient where the effluent has a refractive index under approximately 1.340;
   (c) free from material O.S. elutable in the portions of said gradient where the effluent has a refractive index under approximately 1.340; and
   (d) free from material O.S. elutable only in the portions of said gradient where the effluent has a refractive index over approximately 1.347—
said further limited amplifier material being hereinafter referred to as "amplifier 2."

25. Amplifier material of claim 22, further limited by being substantially:
   (a) entirely O.S. elutable in the portions of said gradient where the effluent has a refractive index between approximately 1.353 and approximately 1.355;
   (b) not O.S. elutable in the portions of said gradient where the effluent has a refractive index under approximately 1.353;
   (c) free from material O.S. elutable in the portions of said gradient where the effluent has a refractive index under approximately 1.353; and
   (d) free from material O.S. elutable only in the portions of said gradient where the effluent has a refractive index over approximately 1.355—
said further limited amplifier material being hereinafter referred to as "amplifier 3."

26. Amplifier material of claim 22, further limited by being substantially:
   (a) entirely O.S. elutable in the portions of said gradient where the effluent has a refractive index between approximately 1.356 and approximately 1.358;
   (b) not O.S. elutable in the portions of said gradient where the effluent has a refractive index under approximately 1.356; and
   (c) free from material O.S. elutable in the portions of said gradient where the effluent has a refractive index under approximately 1.356; and
   (d) free from material O.S. elutable only in the portions of said gradient where the effluent has a refractive index over approximately 1.358—
said further limited amplifier material being hereinafter referred to as "amplifier 4."

27. Amplifier material of claim 22, further limited by being substantially:
   (a) entirely O.S. elutable in the portions of said gradient where the effluent has a refractive index between approximately 1.359 and approximately 1.360;
   (b) not O.S. elutable in the portions of said gradient where the effluent has a refractive index under approximately 1.359;
   (c) free from material O.S. elutable in the portions of said gradient where the effluent has a refractive index under approximately 1.359; and
   (d) free from material O.S. elutable only in the portions of said gradient where the effluent has a refractive index over approximately 1.360—
said further limited amplifier material being hereinafter referred to as "amplifier 5."

28. Amplifier material of claim 22, further limited by being substantially:
   (a) entirely O.S. elutable in the portions of said gradient where the effluent has a refractive index over approximately 1.361;
   (b) not O.S. elutable in the portions of said gradient where the effluent has a refractive index under approximately 1.361; and
   (c) free from material O.S. elutable in the portions of said gradient where the effluent has a refractive index under approximately 1.361—
said further limited amplifier material being hereinafter referred to as "amplifier 6."

29. Human modulator material of claim 20 with the further limitation that said modulator material affects said response by decreasing the speed or magnitude of said response—said further-limited human modulator material being hereinafter referred to as "suppressor material."

30. Suppressor material of claim 29, further limited by being material:
   (a) dialyzable through a dialysis membrane having a nominal molecular weight cutoff of approximately 3500;
   (b) substantially entirely O.S. elutable in the portions of said gradient where the effluent has a refractive index between approximately 1.3600 and approximately 1.3608;
   (c) substantially not O.S. elutable in the portions of said gradient where the effluent has a refractive index under approximately 1.3600;
   (d) substantially free of material O.S. elutable in the portions of said gradient where the effluent has a refractive index under approximately 1.3600; and
   (e) substantially free of material O.S. elutable only in the portions of said gradient where the refractive index is over approximately 1.3608—
said further-limited suppressor material being hereinafter referrred to as "S-suppressor."

31. Suppressor material of claim 29, further limited by being material:
   (a) dialyzable through a dialysis membrane having a nominal molecular weight cutoff of approximately 12,000;

(b) not dialyzable through a dialysis membrane having a nominal molecular weight cutoff of approximately 3500;
(c) substantially entirely chromatographically elutable from hydroxylapatite by ammonium bicarbonate aqueous solution gradient, in the portions of said gradient between approximately 0.1M and approximately 0.15M;
(d) substantially not so elutable below approximately 0.1M;
(e) substantially free of material so elutable below approximately 0.1M; and
(f) substantially free of material so elutable only above approximately 0.15M— said further-limited suppressor material being hereinafter referred to as "L-suppressor."

32. Human modulator material of claim 20, in an effective dosage amount, and in a pharmaceutically acceptable vehicle, thereby comprising a pharmaceutical composition for modulating the response of the immune system of a human body to reintroduction of antigens to which said body has previously been exposed.

33. The composition of claim 32 wherein said human modulator material is amplifier material and said response is modulated by increasing the speed or magnitude thereof.

34. The composition of claim 33 wherein said amplifier material includes at least one member of the group consisting of amplifiers 1 to 6.

35. The composition of claim 32 wherein said human modulator material is suppressor material and said response is modulated by decreasing the speed or magnitude thereof.

36. The composition of claim 35 wherein said suppressor material includes S-suppressor.

37. The composition of claim 35 wherein said suppressor material includes L-suppressor.

38. A method of modulating the immune response of a human body to the reintroduction of antigen to which said human body has previously been exposed, comprising administering to said body human modulator material, in an effective dosage amount, and in a pharmaceutically acceptable vehicle.

39. The method of claim 38 wherein said human modulator material is amplifier material and said response is modulated by increasing the speed or magnitude thereof.

40. The method of claim 39 wherein said amplifier material includes at least one member of the group consisting of amplifiers 1 to 6.

41. The method of claim 38 wherein said human modulator material is suppressor material and said response is modulated by decreasing the speed or magnitude thereof.

42. The method of claim 41 wherein said suppressor material is S-suppressor.

43. The method of claim 41 wherein said suppressor material is L-suppressor.

* * * * *